(12) United States Patent
Kundnani et al.

(10) Patent No.: US 12,620,477 B2

(45) Date of Patent: May 5, 2026

(54) SYSTEM AND METHOD FOR DETECTING LUNG ABNORMALITIES IN A MEDICAL IMAGE

(71) Applicant: Qure.ai Technologies Private Limited, Mumbai (IN)

(72) Inventors: Bunty Kundnani, Mumbai (IN); Sri Anusha Matta, Mumbai (IN); Ayushi Mahendra, Mumbai (IN)

(73) Assignee: Qure.ai Technologies Private Limited, Mumbai (IN)

( * ) Notice: Subject to any disclaimer, the term of this patent is extended or adjusted under 35 U.S.C. 154(b) by 21 days.

(21) Appl. No.: 18/954,618

(22) Filed: Nov. 21, 2024

(65) Prior Publication Data

US 2025/0132019 A1 Apr. 24, 2025

(30) Foreign Application Priority Data

Oct. 20, 2023 (IN) .............................. 202321071661

(51) Int. Cl.
| | |
|---|---|
| *G16H 30/40* | (2018.01) |
| *G06T 7/00* | (2017.01) |

(Continued)

(52) U.S. Cl.
CPC .......... *G16H 30/40* (2018.01); *G06T 7/0012* (2013.01); *G16H 10/60* (2018.01); *G16H 15/00* (2018.01);

(Continued)

(58) Field of Classification Search
CPC ........ G16H 10/60; G16H 50/20; G16H 50/70; G16H 50/30; G16H 15/00; G16H 30/00;

(Continued)

(56) References Cited

U.S. PATENT DOCUMENTS 10,892,056 B2 * 1/2021 Xie .......................... G16H 30/40
11,094,058 B2 * 8/2021 Buckler ................ G06F 18/211

(Continued)

OTHER PUBLICATIONS

Huang, Hanyao, et al. "ChatGPT for shaping the future of dentistry: the potential of multi-modal large language model." International Journal of Oral Science 15.1 (2023): 29 (Year: 2023).*

Primary Examiner — Aaron W Carter
Assistant Examiner — Courtney Joan Nelson

(57) ABSTRACT

The present subject matter relates to a system (100) and a method (300) for detecting lung abnormalities in a medical image (101). The clinical decision support system designed to revolutionize medical diagnosis and treatment recommendations. The system (100) employs a multi-faceted approach, combining data collection, intelligence-based imaging model (207), and language model (208), each playing a pivotal role in enhancing clinical decision-making. Data collection forms the foundation, aggregating diverse data sources including chest images, patient history records, EHS, clinical research data and updated healthcare guidelines. This dataset fuels the training and optimization of intelligent models, ensuring their accuracy and relevance. Integration of the intelligent imaging and language model outputs yields an overall confidence score. The system then furnishes a comprehensive output, encompassing diagnosis, confidence score, and tailored treatment recommendations, facilitating informed clinical decision-making. This innovative framework holds promise in augmenting medical practice, offering enhanced diagnostic precision and personalized treatment guidance.

19 Claims, 4 Drawing Sheets

(51) Int. Cl.
  G16H 10/60   (2018.01)
  G16H 15/00   (2018.01)
  G16H 50/20   (2018.01)
  G16H 50/30   (2018.01)

(52) U.S. Cl.
  CPC ............. G16H 50/20 (2018.01); G16H 50/30
    (2018.01); *G06T 2207/20081* (2013.01); *G06T*
          *2207/30064* (2013.01)

(58) Field of Classification Search
  CPC ........ G16H 30/20; G16H 30/40; G16H 70/60;
    G06F 40/20; G06V 10/82; G06V 10/454;
      G06V 10/764; G06V 10/765; G06V
    10/803; G06T 7/0012; G06T 2207/10081;
      G06T 2207/10132; G06T 2207/20084;
      G06T 2207/30096; G06T 2207/20081;
          G06T 2207/30064
  See application file for complete search history.

(56)       References Cited

U.S. PATENT DOCUMENTS

| | | | |
|---|---|---|---|
| 11,357,582 B1 | 6/2022 | Roh et al. | |
| 11,380,432 B2 | 7/2022 | Glottmann et al. | |
| 11,621,080 B2* | 4/2023 | Cohen ................... | G16B 40/20 |
| | | | 705/3 |
| 11,783,025 B2 | 10/2023 | Molloy et al. | |
| 11,928,186 B2 | 3/2024 | Jadhav et al. | |
| 12,040,075 B2 | 7/2024 | Kalafut et al. | |
| 2021/0327055 A1* | 10/2021 | Putha .................. | G06V 10/774 |
| 2022/0122736 A1* | 4/2022 | Godden ................ | G06N 3/086 |

\* cited by examiner

<u>300</u>

301 collecting data using a data collection module (205), wherein the data corresponds to the medical image (101) and a patient clinical data (102);

302 analysing the collected data by an abnormality detection module (206) by using a hybrid machine learning system

303 detecting lung abnormality by analysing the medical image (101) using an imaging model (207)

304 calculating an image confidence score corresponding to the detected lung abnormality

305 extracting patient related information by using a language model (208)

306 calculating a patient confidence score corresponding to the extracted patient related information

307 generating an abnormality confidence score by combining the image confidence score and the patient confidence score

308 generating an output using an output generation module (210), wherein the output corresponds to the lung abnormality with a comprehensive diagnosis and the abnormality confidence score

SYSTEM AND METHOD FOR DETECTING LUNG ABNORMALITIES IN A MEDICAL IMAGE

CROSS-REFERENCE TO RELATED APPLICATIONS AND PRIORITY

The present application does claim priority from Indian Patent Application number 202321071661 filed on 20 Oct. 2023.

FIELD OF INVENTION

The present subject matter described herein, in general, relates to management of medical abnormalities. More specifically, the present invention relates to detection of lung abnormalities. More particularly, the present invention relates to artificial intelligence (AI) enabled clinical decision support system for detection and management of lung abnormalities on a medical image.

BACKGROUND OF THE INVENTION

This section is intended to introduce the reader to various aspects of art, which may be related to various aspects of the present disclosure that are described or claimed below. This discussion is believed to be helpful in providing the reader with background information to facilitate a better understanding of the various aspects of the present disclosure. Accordingly, it should be understood that these statements in this background section are to be read in this light, and not as admissions of prior art. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Artificial intelligence has revolutionized the healthcare industry by enabling the analysis of patient data, whether in the form of text or medical images. AI-driven systems can swiftly and accurately interpret complex medical records and diagnostic images, aiding healthcare professionals in making more informed decisions. Specifically, the usage of imaging AI for scanning medical images can detect lung abnormalities which may either overlooked or difficult for human experts to identify. However, challenges persist in conventional systems. In text analysis, the sheer volume of unstructured patient data poses difficulties for manual processing, potentially leading to overlooked insights. In image analysis, AI models may require extensive and high-quality datasets for training, which can be scarce. Moreover, concerns about patient data privacy and model interpretability must be addressed to ensure ethical and secure AI integration into healthcare.

Further, Personalization is a cornerstone of effective disease management. Each patient's medical history, genetics, lifestyle, and preferences play a pivotal role in determining the most suitable interventions. Empowering patients with personalized care plans encourage greater adherence to treatment regimens, leading to improved health care and reduced complications.

Traditional healthcare decision support system lacks personalized disease management due to leveraging a single AI model (specifically Imaging AI) for analysing user's medical image. The usage of image-based AI model to identify medical abnormalities are solely based on real-time inputs from the medical image scanned by the imaging AI model. However medical history and current medical condition of the user may have an impact on the medical abnormalities which may or may not be captured in the observations made through scanning the medical image solely. Therefore, a need for analysing the medical history or reports along with user's medical image is expected to perform comprehensive analysis on the user data.

Conventionally healthcare system utilizing the NLP (natural language processing) model has several drawbacks. It often struggles with understanding and interpreting nuanced medical language, leading to potential misinterpretations and errors in clinical documentation. NLP systems can be rigid, requiring constant updates to adapt to evolving medical terminology and language patterns. They may lack the contextual awareness and comprehension capabilities that large language models possess, limiting their ability to extract meaningful insights from complex medical texts. Additionally, building and maintaining NLP-based systems can be resource-intensive and time-consuming, making them less efficient and costly approach.

Further, the absence of large language models (LLMs) such as GPT (generative pre-trained transformer) models in the analysis of patient medical health presents significant shortcomings in healthcare. GPT models, with their natural language understanding capabilities, could greatly enhance the interpretation of unstructured patient data, such as clinical notes and medical histories. Without their use, healthcare providers may struggle to extract valuable insights from these textual sources, potentially missing critical information that could influence patient diagnoses and treatment decisions. GPT models can also aid in automating tasks like medical coding and summarizing complex patient records, saving time and reducing human errors. Nevertheless, the promise of artificial intelligence in healthcare remains significant, offering the potential to enhance diagnosis, treatment, and patient outcomes.

Thus, there exists a need of an innovative approach to detect lung abnormalities in a medical image, that integrates hybrid Artificial Intelligence (AI) technologies with personalized patient diagnosis and care. Furthermore, this holistic framework combines data-driven insights with empathetic human interactions to create a comprehensive solution that addresses the complexities of health and helps to enhance patient outcomes and quality of life.

SUMMARY OF THE INVENTION

Before the present system and device and its components are described, it is to be understood that this disclosure is not limited to the system and its arrangement as described, as there can be multiple possible embodiments which are not expressly illustrated in the present disclosure. The present disclosure overcomes one or more shortcomings of the prior art and provides additional advantages discussed throughout the present disclosure. Additional features and advantages are realized through the techniques of the present disclosure. It is also to be understood that the terminology used in the description is for the purpose of describing the versions or embodiments only and is not intended to limit the scope of the present application. This summary is not intended to identify essential features of the claimed subject matter nor is it intended for use in detecting or limiting the scope of the claimed subject matter.

In one embodiment of the present disclosure, a system for the detection of lung abnormalities in a medical image is disclosed. The system includes a memory and a processor coupled with the memory. The processor may be configured to execute programmed instructions stored in the memory. Further, the system may comprise a data collection module. In one embodiment, data collected by the data collection module may correspond to a medical image and a patient clinical data. Further, the system may comprise an abnormality detection module for identifying lung abnormalities based on the collected data. The abnormality detection module may be configured to use a hybrid machine learning system for identifying lung abnormalities based on the collected data. In one exemplary embodiment, the hybrid machine learning system may correspond to combination of an imaging model and a large language model (LLM). Further, the hybrid machine learning system may comprise a step of detecting lung abnormality by analysing the medical image using the imaging model. Further, the hybrid machine learning system may comprise a step of calculating an image confidence score corresponding to the detected lung abnormality. Further, the hybrid machine learning system may comprise a step of extracting patient related information by using a language model. Further, the hybrid machine learning system may comprise a step of calculating a patient confidence score corresponding to the extracted patient related information. Further, the hybrid machine learning system may comprise a step of generating an abnormality confidence score by combining the image confidence score and the patient confidence score, enhancing the reliability of the diagnosis. The abnormality confidence score may correspond to overall confidence in the abnormality being detected and the diagnosis/treatment pathway being provided. Furthermore, the system may comprise an output generation module for generating an output. The generated output may combine the output of both the imaging model and the large language model (LLM). The generated output may correspond to the lung abnormality with a comprehensive diagnosis and the abnormality confidence score. Further, the output generated by the output generation module may corresponds to personalized treatment and diagnosis recommendation based on patient medical history and clinical data analyzed by the LLM. In an exemplary embodiment, the output may correspond to an abnormality diagnostic report. The abnormality diagnostic report may comprise the medical image with one or more visual bounding boxes to annotate the one or more lung abnormalities detected by the system. In an embodiment, the abnormality detection report is configured to be extracted in multiple readable formats, which includes the detected abnormalities in greater details including but not limited to the medical image with one or more visual bounding boxes, corresponding labels to annotate the one or more detected lung abnormalities, a diagnosis report, a treatment recommendation report, the abnormality confidence score and a brief explanation on relevance of the abnormality confidence score. This system holds significant potential for enhancing the accuracy and efficiency of lung abnormality detection in medical practice.

In one embodiment, the system may utilize the medical image data in various forms namely x-ray scans, CT scans, MRI scans, ultrasound images, and more. Additionally, the patient clinical data used by the system may encompass a wide range of sources such as patient history records, electronic health records (EHR), clinical research data, and updated medical device or healthcare guidelines available on public platforms, allowing for a comprehensive assessment of the patient's health. The clinical research data incorporated into the system may be specifically tailored to the domain of lung abnormalities, enhancing its relevance and precision. In an embodiment, the abnormality detection module may be configured to train the imaging model and the language model using the data collected by the data collection module.

In another embodiment, the imaging model may correspond to a deep learning algorithm for analysing the medical images for detecting lung abnormalities. The lung abnormalities detected using the imaging model may corresponds to one of Asthma, Chronic obstructive pulmonary disease (COPD), Bronchiectasis, Bronchitis, pneumothorax, atelectasis, lung inflammation, Pulmonary fibrosis, Sarcoidosis, Lung cancer, Lung Infection (Pneumonia), Hyperinflation/Emphysema, Consolidation, Opacity, Scoliosis, Fibrosis, Tuberculosis screening, Atelectasis, Reticulo-nodular pattern, Nodules, Cavity, Calcification, Linear Opacities, Lung Nodule Malignancy, Covid-19 risk and a combination thereof. Further, the imaging model, along with the lung abnormalities, may detect other abnormalities, including but not limited to, Cardiomegaly, Degenerative spine conditions, Prominence in Hilar region, Blunted Costophrenic Angle, Pleural effusion, Tracheal shift, Pneumothorax, Elevated Hemidiaphragm, Pneumoperitoneum, Rib Fractures, Mediastinal Widening, Presence of Tracheal Tube, Presence of Gastric Tube, Placement of Tracheal Tube, Placement of Gastric Tube. Along with detecting the lung abnormalities, the imaging model may be configured to calculate the image confidence score based on the analysis of the medical image.

In yet another embodiment, the language model may correspond to one of Generative Pre-trained Transformer (GPT) model, a Large Language Model (LLM), and a combination thereof, for extracting the patient related information. The patient related information extracted by the language model may correspond to one of identified risk factors, underlying cause of lung disease and a combination thereof. Along with extraction of patient related information, the language model may be configured to calculate the patient confidence score corresponding to the extracted patient related information. Further, the language model may be configured to suggest treatment recommendation to the user based on extracted patient related information from the patient history records, electronic health records (EHR), the clinical research data, and the updated medical device or healthcare guidelines available on the public platforms.

In yet another embodiment, the system may enable monitoring the lung abnormalities over time. Monitoring the lung abnormalities may help in tracking disease progression and adjustment of treatment plan. Further, the system may be configured to provide accurate and up-to-date lung abnormality diagnosis based on continuously learning from clinical evidence over time and adapting the system accordingly. The system is configured to be self-evolving the analysis, to be performed by the system, based on the output analysis previously resulted by the system and any subsequent feedback provided, to the system, by the user.

In another embodiment of the present disclosure, a method for detecting lung abnormalities in a medical image is disclosed. The method is a comprehensive approach that involves several key stages. The method may comprise a step for collecting data using a data collection module. The collected data may correspond to the medical image and the patient clinical data. Further, the method may comprise a step of analysing the collected data by an abnormality detection module using a hybrid machine learning system. The hybrid machine learning system may correspond to combination of an imaging model and a large language model (LLM). Further, the hybrid machine learning system may comprise a step of detecting lung abnormality by analysing the medical image using the imaging model. Further, the hybrid machine learning system may comprise a step of calculating an image confidence score corresponding to the detected lung abnormality. Further, the hybrid machine learning system may comprise a step of extracting patient related information by using a language model. Further, the hybrid machine learning system may comprise a step of calculating a patient confidence score corresponding to the extracted patient related information. Further, the hybrid machine learning system may comprise a step of generating an abnormality confidence score by combining the image confidence score and the patient confidence score. The abnormality confidence score may correspond to overall confidence in the abnormality being detected and the diagnosis/treatment pathway being provided. Furthermore, the method may comprise a step of synthesizes this information into a comprehensive output, providing healthcare professionals with a holistic evaluation that incorporates both the image analysis and clinical data, thus improving the accuracy and confidence in detecting lung abnormalities. The generated output may combine the output of both the imaging model and the large language model (LLM). The generated output may correspond to the lung abnormality with a comprehensive diagnosis and the abnormality confidence score. Further, the output generated by the output generation module may corresponds to personalized treatment and diagnosis recommendation based on patient medical history and clinical data analyzed by the LLM. In an exemplary embodiment, the output may correspond to an abnormality diagnostic report. The abnormality diagnostic report may comprise the medical image with one or more visual bounding boxes to annotate the one or more lung abnormalities detected by the system. In an embodiment, the abnormality detection report is configured to be extracted in multiple readable formats, which includes the detected abnormalities in greater details including but not limited to the medical image with one or more visual bounding boxes, corresponding labels to annotate the one or more detected lung abnormalities, a diagnosis report, a treatment recommendation report, the abnormality confidence score and a brief explanation on relevance of the abnormality confidence score.

In one embodiment, the method may include various aspects of data collection and analysis. A medical image data collection encompasses a wide range of modalities such as x-ray scans, CT scans, MRI scans, and ultrasound images, and more, while a patient clinical data collection includes patient history records, electronic health records (EHR), clinical research data, particularly focused on lung abnormalities, and updated medical device or healthcare guidelines available on public platforms. The analysis of medical images is carried out using deep learning algorithms within the imaging model, and the image confidence score is calculated based on this analysis. Further, the patient clinical data analysis may include GPT or large language models (LLM), extracting patient relevant information from unstructured clinical text and recommending treatment options, with a patient confidence score calculated accordingly. The overall abnormality confidence score is determined through a combination formula involving both the imaging and language models. Ultimately, the method may generate a comprehensive output including a diagnosis, confidence score, and tailored treatment recommendations based on the collected data, enhancing clinical decision-making in pulmonary health.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

FIG. 3 illustrates a flowchart describing a method (300) for detecting lung abnormalities in a medical image (101) using a hybrid machine learning system, in accordance with an embodiment of the present subject matter.

DETAILED DESCRIPTION OF THE INVENTION

Figure 1:
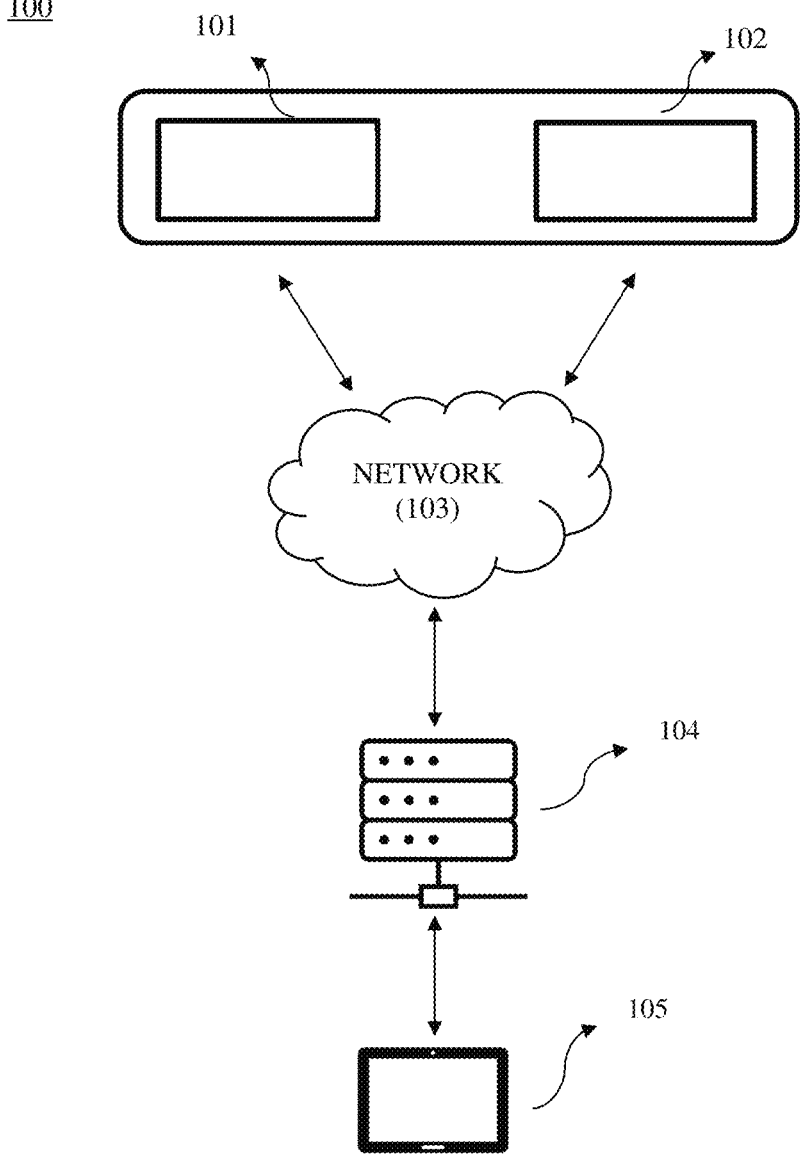
FIG. 1 illustrates a block diagram describing a system (100) for detecting lung abnormalities in a medical image (101), in accordance with an embodiment of a present subject matter.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the features, structures or characteristics may be combined in any suitable manner in one or more embodiments.

The words "comprising," "having," "containing," and "including," and other forms thereof, are intended to be equivalent in meaning and be open ended in that an item or items following any one of these words is not meant to be an exhaustive listing of such item or items or meant to be limited to only the listed item or items. It must also be noted that, the singular forms "a" "an" and "the" include plural references unless the context clearly dictates otherwise. Although any methods similar or equivalent to those described herein can be used in the practice or testing of embodiments of the present disclosure, the exemplary methods are described. The disclosed embodiments are merely exemplary of the disclosure, which may be embodied in various forms.

The integration of artificial intelligence (AI) techniques in medical healthcare has revolutionized the industry by leveraging advanced algorithms and machine learning to analyse vast datasets, enhance diagnostic accuracy, personalize treatment plans, and streamline administrative processes.

Further, the transformer based deep learning models such as large language models (LLMs), GPT (generative pre-trained transformer) model has advanced medical healthcare systems by leveraging its natural language understanding capabilities. It can efficiently analyse vast volumes of medical literature, patient records, and clinical notes to extract valuable insights and assist in diagnosis, treatment recommendations, and medical research. GPT's ability to understand and generate human-like text and adapt to evolving medical terminology makes it a powerful tool for enhancing communication among healthcare professionals and patients.

However, a conventional healthcare system based on the NLP (natural language processing) model has several drawbacks. It often struggles with understanding and interpreting nuanced medical language, leading to potential misinterpretations and errors in clinical documentation. NLP systems can be rigid, requiring constant updates to adapt to evolving medical terminology and language patterns. They may lack the contextual awareness and comprehension capabilities that large language models possess, limiting their ability to extract meaningful insights from complex medical texts. Additionally, building and maintaining NLP-based systems can be resource-intensive and time-consuming, making them less efficient and cost-effective compared to newer LLM approaches in the healthcare.

In the light of the above-mentioned limitations, the large language models (LLMs) like GPT offer significant advantages over traditional natural language processing (NLP) methods in the context of detecting lung abnormalities in healthcare. LLMs excel at understanding and contextualizing complex medical language, allowing them to analyse unstructured clinical text with greater accuracy. They adapt to evolving medical terminology and language patterns, reducing the need for constant rule-based updates. LLMs can also integrate multimodal data, such as medical images and clinical notes, for a more comprehensive analysis, improving diagnostic precision. Furthermore, these models can be fine-tuned for specific healthcare tasks, enhancing their performance. Overall, LLMs offer a more versatile, adaptable, and powerful approach to lung abnormality detection in healthcare.

In one non-limiting embodiment, a system for the detection of lung abnormalities in the medical image, by using a hybrid machine learning system is disclosed. The system may include variety of data collected in form of a medical image data and a patient clinical data. The hybrid machine learning system corresponds to combination of deep learning-based imaging model and LLM based language model, which helps in identifying the lung abnormalities from the medical image in an intelligent manner. The system may be capable of learning from its operation, improving its abnormality detection capabilities over time. The system can learn from each interaction, continuously refining its understanding of individual medical parameters and corresponding effects on the lungs, and ultimately, the efficiency of the lung abnormality it generates.

Figure 2:
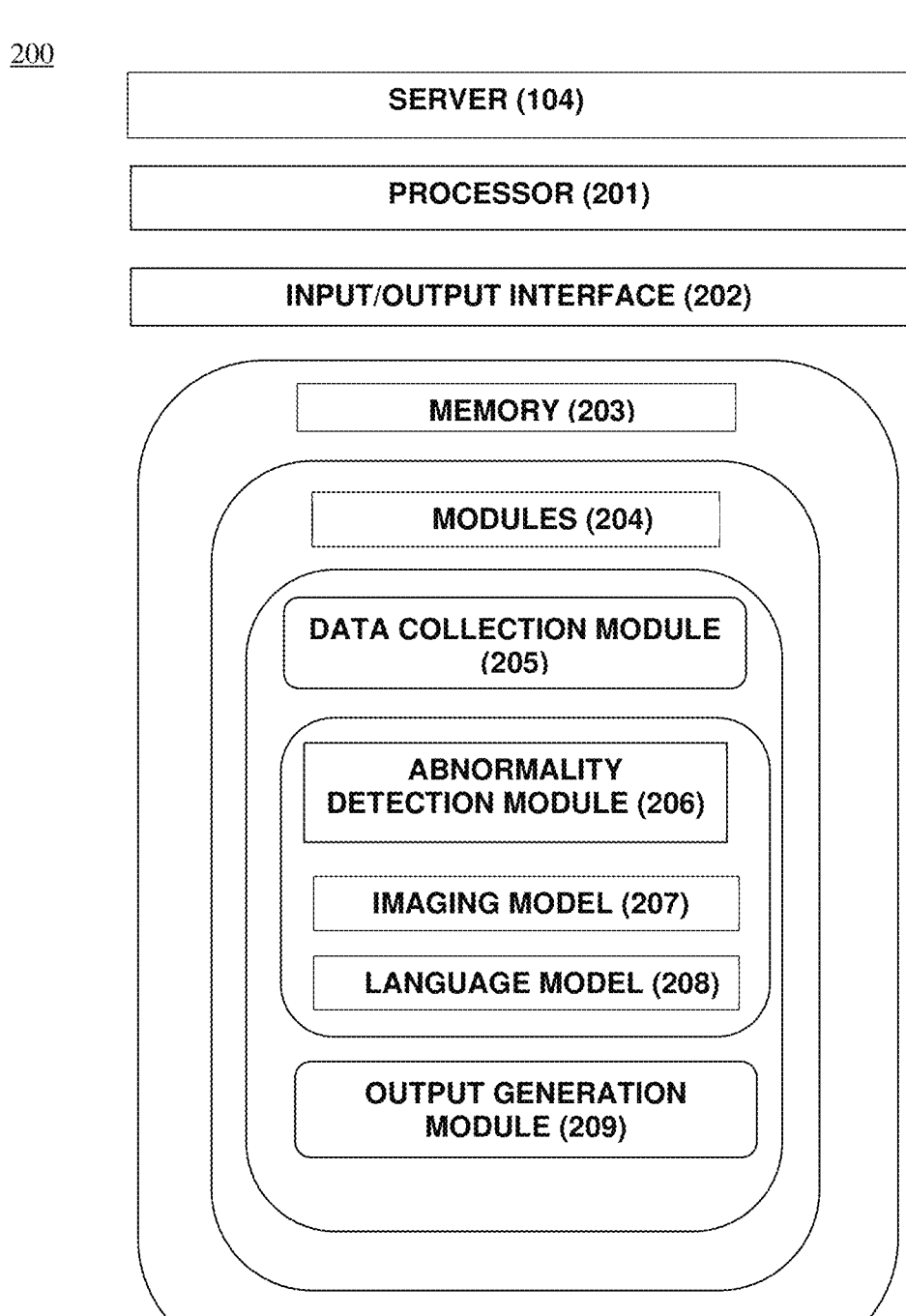
FIG. 2 illustrates a block diagram (200) showing an overview of a server (104) for detecting lung abnormalities in a medical image (101), in accordance with an embodiment of a present subject matter.

Now referring to FIG. 1, a block diagram describing a system (100) for detecting lung abnormalities in a medical image (101), is illustrated in accordance with an embodiment of a present subject matter. The system (100) may include variety of data collected in form of a medical image (101) data and a patient clinical data (102). The collected data is coupled with the server (104) via a network (103) connection. Further, considering that the system (100) is implemented on a server (104), it may be understood that the system (100) may be accessed via a variety of user devices (105). The user device (105) may correspond to an interface which enables the user to interact with the system (100). The user device (105) may comprise one selected from a group consisting of a cell phone, personal digital assistant (PDA), laptop computer, stationary personal computer, IPTV remote control, web tablet, laptop computer, pocket PC, a television set capable of receiving IP based video services and mobile IP device. In an embodiment, the system (100) may be configured to receive user data from one or more users, via the user device (105). The collected data may be in form of the medical image (101) data and the patient clinical data (102). In an exemplary embodiment, the medical image (101) corresponds to a chest image data in form of one of x-ray scans, CT scans, MRI scans, ultrasound images, and a combination thereof. In another exemplary embodiment, the patient clinical data (102) corresponds to one of patient history records, an electronic health records (EHR), clinical research data, updated medical device or healthcare guidelines available on public platforms, and a combination thereof. The clinical research data corresponds to research information published in domain of lung abnormalities. Both medical image (101) and the patient clinical data (102) may be used by the system (100) to detect ling abnormalities with an accurate and comprehensive diagnosis of the patient. In an embodiment, medical image (101) and the patient clinical data (102) are collected by the server (104) via the network (103), is transmitted to a memory (203) (as illustrated in FIG. 2) for storage. Further, the functionality and other characteristics of the server (104) would be provided in description of FIG. 2.

In yet another embodiment, the collected data (101, 102), the server (104) and the user device (105) may communicate with each other via the network (103). In one implementation, the network (103) may be a wireless network, a wired network, or a combination thereof. The network (103) can be implemented as one of the different types of networks, such as intranet, local area network (LAN), wide area network (WAN), the internet, and the like. The network (103) may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network (103) may include a variety of network devices, including routers, bridges, servers, computing devices, storage devices, and the like.

In another embodiment, the network (103) may include any one of the following: a cable network, the wireless network, a telephone network (e.g., Analog, Digital, POTS, PSTN, ISDN, xDSL), a cellular communication network, a mobile telephone network (e.g., CDMA, GSM, NDAC, TDMA, E-TDMA, NAMPS, WCDMA, CDMA-2000, UMTS, 3G, 4G, 5G, 6G), a radio network, a television network, the Internet, the intranet, the local area network (LAN), the wide area network (WAN), an electronic positioning network, an X.25 network, an optical network (e.g., PON), a satellite network (e.g., VSAT), a packet-switched network, a circuit-switched network, a public network, a private network, and/or other wired or wireless communications network configured to carry data.

The system (100) can be implemented using hardware, software, or a combination of both, which includes using where suitable, one or more computer programs, mobile applications, or "apps" by deploying either on-premises over the corresponding computing terminals or virtually over cloud infrastructure. The system (100) may include various micro-services or groups of independent computer programs which can act independently in collaboration with other micro-services. The system (100) may also interact with a third-party or external computer system. Internally, the system (100) may be the central processor of all requests for transactions by the various actors or users of the system. A critical attribute of the system (100) is that it can concurrently and instantly complete an online transaction by a system user in collaboration with other systems.

Now, referring to FIG. 2, a block diagram (200) showing an overview of the server (104) for detecting lung abnormalities in the medical image (101), is illustrated in accordance with an embodiment of a present subject matter. The server (104) includes a processor (201), an input/output (I/O) interface (202), and the memory (203). The processor (201) is coupled with the memory (203). The processor (201) is configured to execute programmed instructions stored in the memory (203). The processor, in one embodiment, may comprise a standard microprocessor, microcontroller, central processing unit (CPU), distributed or cloud processing unit, state machines, logic circuitries, and/or any devices that manipulate signals based on operational instructions and/or other processing logic that accommodates the requirements of the present invention.

Further, the I/O interface (202) is an interface to other components of the server (104) and the system (100). The I/O interface (202) may include a variety of software and hardware interfaces, for example, a web interface, a graphical user interface, and the like. The I/O interface (202) may allow the system (100) to interact with the user directly or through the user devices (105). Further, the I/O interface (202) may enable the system (100) to communicate with other computing devices, such as web servers and external data servers (not shown). The I/O interface (202) can facilitate multiple communications within a wide variety of networks and protocol types, including wired networks, for example, LAN, cable, etc., and wireless networks, such as WLAN, cellular, or satellite. The I/O interface (202) may include one or more ports for connecting a number of devices to one another or to another server. In one embodiment, the I/O interface (202) allow the server (104) to be logically coupled to another user device (105), some of which may be built in. Illustrative components include tablets, mobile phones, scanner, printer, wireless device, etc. Further, the processors (201) can read data from various entities such as memory (203) or I/O interface (202). The processor's (201) primary functions encompass data acquisition, wherein it gathers medical image data (101) and patient clinical data (102). Following this, the collected data undergoes analysis through specialized modules, and the system (100) computes a overall confidence score. Ultimately, it generates an output, which typically includes a diagnosis or evaluation on the lung abnormalities, informed by the comprehensive analysis of both the medical image and the patient clinical data. In an exemplary embodiment, the output may correspond to an abnormality diagnostic report. The abnormality diagnostic report may comprise the medical image with one or more visual bounding boxes to annotate the one or more lung abnormalities detected by the system (100). In an embodiment, the abnormality detection report is configured to be extracted in multiple readable formats, which includes the detected abnormalities in greater details including but not limited to the medical image with one or more visual bounding boxes, corresponding labels to annotate the one or more detected lung abnormalities, a diagnosis report, a treatment recommendation report, the abnormality confidence score and a brief explanation on relevance of the abnormality confidence score.

The memory (203) may include any computer-readable medium or computer program product known in the art including, for example, volatile memory, such as static random-access memory (SRAM) and dynamic random-access memory (DRAM), and/or non-volatile memory, such as read only memory (ROM), erasable programmable ROM, flash memories, hard disks, Solid State Disks (SSD), optical disks, magnetic tapes, memory cards, virtual memory and distributed cloud storage. The memory (203) may be removable, non-removable, or a combination thereof. The memory (203) may include routines, programs, objects, components, data structures, etc., which perform particular tasks or implement particular abstract data types. The memory (203) may include programs or coded instructions that supplement applications and functions of the system (100). In one embodiment, the memory (203), amongst other things, serves as a repository for storing data processed, received, and generated by one or more of the programs or the coded instructions. In yet another embodiment, the memory (203) may be managed under a federated structure that enables adaptability and responsiveness of the server (104). The memory further may include various modules (204) namely a data collection module (205), an abnormality detection module (206) and an output generation module (209). The abnormality detection module (206) may further include an imaging model (207) and a language model (208). In one embodiment, the server (104) utilizes the processor (201) for executing the various modules (204) stored in the memory (203).

The data collection module (205) is configured to collect data corresponding to the medical image (101) and the patient clinical data (102). In an exemplary embodiment, the medical image (101) corresponds to a chest image data in form of one of x-ray scans, CT scans, MRI scans, ultrasound images, and a combination thereof. In another exemplary embodiment, the patient clinical data (102) corresponds to one of patient history records, an electronic health records (EHR), clinical research data, updated medical device or healthcare guidelines available on public platforms and a combination thereof. The clinical research data corresponds to research information published in domain of lung abnormalities. The data collected by the data collection module (205) is utilized by the abnormality detection module (206) for detecting the lung abnormalities. In one exemplary embodiment, the abnormality detection module (206) is implemented by using a hybrid machine learning system. In one implementation, the abnormality detection module (206) analyses the imaging data (101) and the patient clinical data (102) by using the hybrid machine learning system and generates an output regarding detection of lung abnormalities in the medical images with comprehensive diagnosis. In an embodiment, the abnormality detection module (206) may utilize the processor (201) to implement the hybrid machine learning system. The hybrid machine learning system corresponds to combination of the imaging model (207) and the language model (208). In a related implementation, the abnormality detection module (206) is configured to train the hybrid machine learning system, including the imaging model (207) and the language model (208), using the imaging data (101) and the patient clinical data (102).

In one embodiment, the imaging model (207), with the help of processor (201), is configured to analyse the medical images (101) to detect lung abnormality based on the medical image (101). In one embodiment, the imaging model (207) corresponds to a deep learning algorithm. The imaging model (207) may further be configured to calculate an image confidence score corresponding to the detected lung abnormality. The image confidence score gives the probability of detected lung abnormality in the medical image (101) being detected correctly by the algorithm of the imaging model (207) and may be given as a percentage. Further, the lung abnormalities detected using the imaging model (207) corresponds to one of Asthma, Chronic obstructive pulmonary disease (COPD), Bronchiectasis, Bronchitis, pneumothorax, atelectasis, lung inflammation, Pulmonary fibrosis, Sarcoidosis, Lung cancer, Lung Infection (Pneumonia), Hyperinflation/Emphysema, Consolidation, Opacity, Scoliosis, Fibrosis, Tuberculosis screening, Atelectasis, Reticulo-nodular pattern, Nodules, Cavity, Calcification, Linear Opacities, Lung Nodule Malignancy, Covid-19 risk and a combination thereof. Further, the imaging model (207), along with the lung abnormalities, may detect other abnormalities, including but not limited to, Cardiomegaly, Degenerative spine conditions, Prominence in Hilar region, Blunted Costophrenic Angle, Pleural effusion, Tracheal shift, Pneumothorax, Elevated Hemidiaphragm, Pneumoperitoneum, Rib Fractures, Mediastinal Widening, Presence of Tracheal Tube, Presence of Gastric Tube, Placement of Tracheal Tube, Placement of Gastric Tube.

In one embodiment, the language model (208), with the help of processor (201), is configured to analyse the patient clinical data (102) to extract patient related information. In a related embodiment, the language model (208) is configured to extract patient relevant information from an unstructured clinical text and to provide treatment options. In one embodiment, the language model (208) may correspond to one of Generative Pre-trained Transformer (GPT) model, a Large Language Model (LLM), and a combination thereof. Further, the language model (208) is configured to calculate a patient confidence score corresponding to the extracted patient related information. The patient confidence score gives the probability of extracted patient related information from the patient clinical data (102) being detected correctly by the algorithm of the language model (207) and may be given as a percentage. The patient confidence score may also showcase confidence in the diagnosis and treatment pathway recommended by the system (100). In one embodiment, the patient related information extracted by the language model (208) corresponds to one of identified risk factors, underlying cause of lung disease and a combination thereof.

In an embodiment, the abnormality detection module (206) is configured to generate an abnormality confidence score by combining the image confidence score and the patient confidence score. The abnormality confidence score may correspond to overall confidence in the abnormality being detected and the diagnosis/treatment pathway being provided. The abnormality confidence score may cover a comprehensive aspect of the lung abnormality detected based on the patient's medical image, patient history records, the EHR, the clinical research data, and updated medical device or healthcare guidelines available on public platforms.

Figure 4:
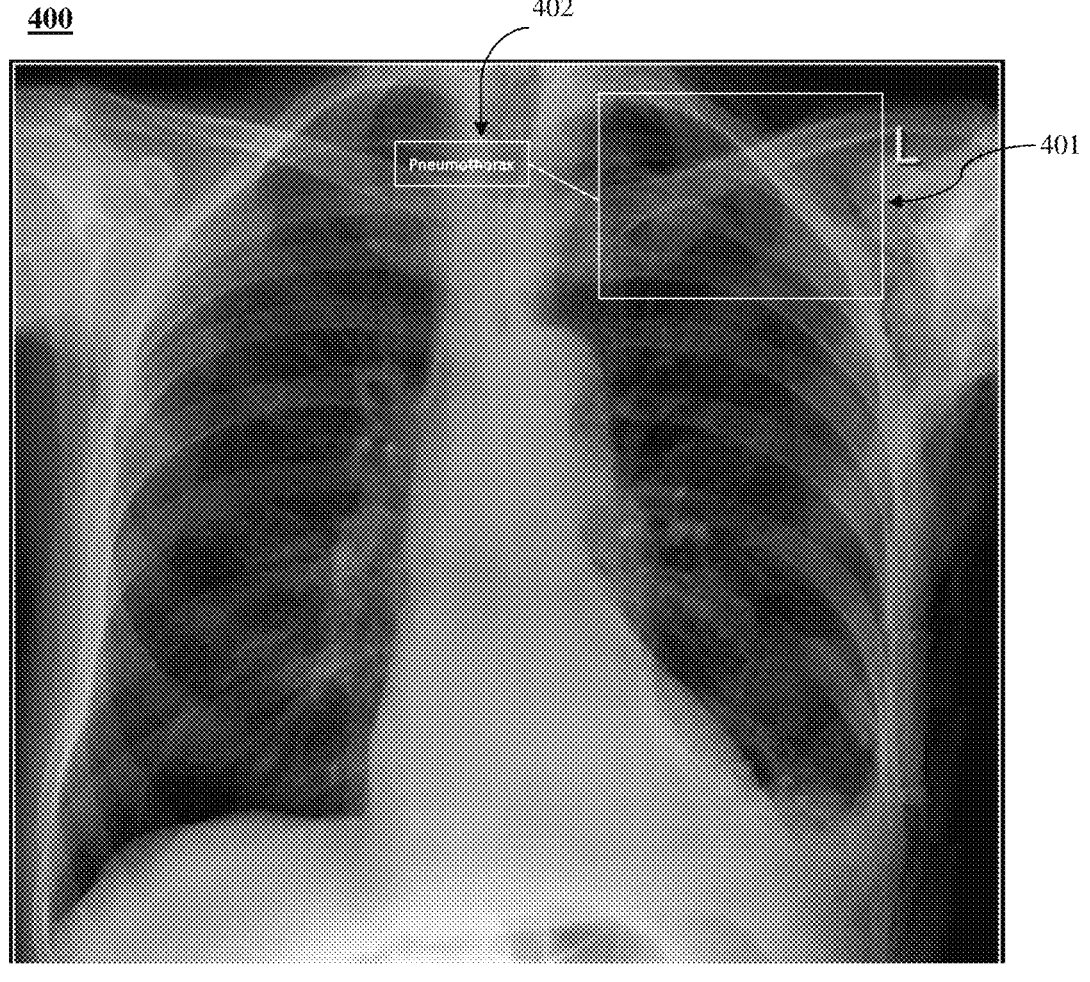
FIG. 4 illustrates a lung abnormality report (400) generated by an output generation module (209) of the system (100) for detecting lung abnormalities in the medical image (101), in accordance with an embodiment of the present subject matter.

Further, the output generation module (209) is configured to producing a comprehensive output that encompasses the comprehensive diagnosis on lung abnormality, the abnormality confidence score, and the customized and personalized treatment recommendations based on the collected data. The generated output may combine the output of both the imaging model (207) and the language model (208). In an exemplary embodiment, the output may correspond to an abnormality diagnostic report. The abnormality diagnostic report (400) (as shown in FIG. 4) may comprise the medical image with one or more visual bounding boxes (401) to annotate the one or more lung abnormalities (402) detected by the system (100). In an embodiment, the abnormality detection report (400) is configured to be extracted in multiple readable formats, which includes the detected abnormalities in greater details including but not limited to the medical image with one or more visual bounding boxes (401), corresponding labels (402) to annotate the one or more detected lung abnormalities, a diagnosis report (not illustrated), a treatment recommendation report (not illustrated), the abnormality confidence score (not illustrated) and a brief explanation on relevance of the abnormality confidence score (not illustrated).

In another embodiment, the server (104) may present the comprehensive output regarding the lung abnormality on the user device (105) of the system (100). In yet another embodiment, the system (100) may enables monitoring the lung abnormalities over time, which may help in tracking disease progression over time and adjustment of treatment plan. In yet another embodiment, the system (100) may enables providing accurate and up-to-date lung abnormality diagnosis based on continuously learning from clinical evidence over time and adapting the system (100) accordingly. The disclosed system (100) is configured to be self-evolving the analysis, to be performed by the system (100), based on the output analysis previously resulted by the system (100) and any subsequent feedback provided, to the system (100), by the user.

Although the present disclosure is explained considering that the system (100) is implemented on a server, it may be understood that the system (100) may be implemented in a variety of computing systems, such as a laptop computer, a desktop computer, a notebook, a workstation, a virtual environment, a mainframe computer, a server, a network server, a cloud-based computing environment. It will be understood that the system (100) may be accessed by multiple users through one or more user devices. In one implementation, the system (100) may comprise the cloud-based computing environment in which the user may operate individual computing systems configured to execute remotely located applications. Examples of the user devices may include, but are not limited to, a portable computer, a personal digital assistant, a handheld device, and a workstation.

Now referring to FIG. 3, a flowchart describing a method (300) for detecting lung abnormalities in a medical image (101), is illustrated in accordance with an embodiment of the present subject matter. The method (300) is structured as a step-by-step process. The method (300) comprises a step for collecting (301) relevant data, including the medical image (101) and a patient's clinical data (102). Subsequently, the method (300) comprises a step of analysing (302) the collected data by an abnormality detection module (206), by using a hybrid machine learning system. Further, the method (300) comprises a step of detecting (303) lung abnormality by analysing the medical image (101) using an imaging model (207). Further, the method (300) comprises a step of calculating (304) an image confidence score corresponding to the detected lung abnormality by the imaging model (207). Further, the method (300) comprises a step of extracting (305) patient related information by using a language model (208). The method (300) may further comprise a step of calculating (306) a patient confidence score corresponding to the extracted patient related information by the language model (208). Further, the method (300) comprises a step of generating (307) an abnormality confidence score by combining the image confidence score and the patient confidence score. The abnormality confidence score may correspond to overall confidence in the abnormality being detected and the diagnosis/treatment pathway being provided. Further, the method (300) comprises a step of generating (308) an output using an output generation module (209). The output corresponds to the lung abnormality with a comprehensive diagnosis and the abnormality confidence score. providing healthcare professionals with a holistic evaluation that incorporates both the image analysis and clinical data, thus improving the accuracy and confidence in detecting lung abnormalities. The generated output may combine the output of both the imaging model (207) and the language model (208). In an exemplary embodiment, the output may correspond to an abnormality diagnostic report. The abnormality diagnostic report (400) (as shown in FIG. 4) may comprise the medical image with one or more visual bounding boxes (401) to annotate the one or more lung abnormalities (402) detected by the system (100). In an embodiment, the abnormality detection report (400) is configured to be extracted in multiple readable formats, which includes the detected abnormalities in greater details including but not limited to the medical image with one or more visual bounding boxes (401), corresponding labels (402) to annotate the one or more detected lung abnormalities, a diagnosis report (not illustrated), a treatment recommendation report (not illustrated), the abnormality confidence score (not illustrated) and a brief explanation on relevance of the abnormality confidence score (not illustrated).

In one embodiment, the method (300) may include various aspects of data collection module (205) and abnormality detection module (206). Further, the medical image (101) data collected encompasses a wide range of modalities such as x-ray scans, CT scans, MRI scans, and ultrasound images, and more, while the patient clinical data (102) collection includes patient history records, electronic health records (EHR), clinical research data, particularly focused on lung abnormalities, and updated medical device or healthcare guidelines available on the public platforms. The analysis of medical images is carried out using deep learning algorithms within the image model, and the confidence score is calculated based on this analysis. Further, the patient clinical data (102) analysis may include GPT and Large Language Models (LLM), extracting relevant information from unstructured clinical text and recommending treatment options, with a confidence score calculated accordingly. The overall confidence score is determined through a combination formula involving both the image and language models. Ultimately, the method may generate a comprehensive output including a diagnosis, confidence score, and tailored treatment recommendations based on the collected data, enhancing clinical decision-making in pulmonary health. The generated output may combine the output of both the imaging model (207) and the language model (208). In an exemplary embodiment, the output may correspond to an abnormality diagnostic report.

Now referring to FIG. 4, the lung abnormality report (400) generated by an output generation module (209) of the system (100) for detecting lung abnormalities in the medical image (101), is illustrated, in accordance with an embodiment of the present subject matter. The lung abnormality report (400) may provide the medical image (101) with one or more visual bounding boxes (401). The visual bounding box (401) corresponds to localize one or more regions in the medical image (101) which may be affected by the lung abnormalities as detected by the system (100). In an instance, there may be more than one boxes (401) may be visualized in the medical image (101) which represents the more than one lung abnormalities as detected by the system (100). In another instance the one or more visual bounding boxes (401) may represent different other abnormalities along with the lung abnormality detected by the system (100). In one exemplary embodiment, the one or more visual bounding box (401) corresponds to a rectangular shape box representing the affected area in the medical image (101). The visual bounding box (401) may correspond to any other shape boundaries representing the affected area in the medical image (101). Further, the lung abnormality report (400) may provide the medical image (101) with labels (402) to annotate the one or more lung abnormalities corresponding to each visual bounding box (401). The label (402) may correspond to name of the lung abnormality detected by the system (100).

In one embodiment, deep learning (may also be called as deep learning techniques) may be a part of a machine learning family. The deep learning techniques may comprise multiple layers in a network. The deep learning techniques may comprise a Convolutional Neural Network (CNN) technique. The deep learning techniques may use a trained data model for an operation. The trained data model comprises historical information, chest X-rays of a set of patients, medical history of the set of patients, the information associated to the nodules for the set of patients. It may be noted that the trained data model may information associated with other abnormalities, to be identified from the chest X-rays. It may be noted that the trained data model may be trained using a continuous learning approach like Reinforcement Learning techniques. The trained data model may correspond to data learned by the system to operate efficiently. The trained data model may enable an accurate operation of the deep learning techniques. In one aspect, the historical data may comprise historical clinical reports and historical chest X-rays associated with the set of patients. In an example, the set of patients may comprise patients suffering from lung abnormalities. In another aspect, the historical data may comprise a previous clinical report and a previous chest X-ray of the patient.

In another embodiment, the utilization of Large Language Models (LLMs) in detecting lung abnormalities represents a transformative advancement in healthcare. LLMs excel at processing and understanding vast amounts of unstructured clinical text, enabling them to extract crucial insights from medical reports, patient histories, research data related to pulmonary health, and updated medical device or healthcare guidelines available on the public platforms. By harnessing their natural language processing capabilities, LLMs can assist medical professionals in rapidly identifying subtle patterns and anomalies in clinical narratives. This, in turn, enhances diagnostic accuracy and provides valuable decision support, ultimately contributing to earlier detection and more effective management of lung abnormalities, thereby improving patient outcomes and streamlining healthcare workflows.

In one aspect, LLM refers to the broader category of large-scale language models that includes GPT as well as other models like BERT (Bidirectional Encoder Representations from Transformers), XLNet, ROBERTa, and more. These models share the common characteristic of being pre-trained on massive text corpora and can be fine-tuned for specific natural language processing tasks.

Overall, this system leverages LLM (large language model) and deep learning techniques to enhance lung abnormalities detection with advanced data analysis.

EXAMPLE

Normal scenario (Unaided): If a patient comes to the hospital with flu-like symptoms and wheezing, the healthcare professional would first take the patient's medical history, including any existing medical conditions, allergies, and medications. They would then perform a physical examination, which may include listening to the patient's chest with a stethoscope and ordering diagnostic tests such as chest x-rays.

Using Disclosed System (Aided): The mentioned technology could be used to assist in the diagnosis process. The healthcare professional would input the patient's medical history, test results, and any other relevant clinical data into the device. The AI imaging model would analyse the chest x-ray scan to detect any abnormalities, such as pneumonia or lung inflammation, while the language model would analyse the patient's medical history to identify any risk factors or potential underlying causes of the wheezing.

The system would then generate a confidence score that combines the scores generated by the AI imaging model and the language model, providing additional diagnostic support to the healthcare professional. Based on the results, the healthcare professional could then make a more informed diagnosis and recommend appropriate treatment options.

Overall, the system could help healthcare professionals in making a more accurate and timely diagnosis of lung disease, leading to better patient outcomes and potentially reducing the overall cost of care.

The system (100) as disclosed in the disclosure may help in clinical decision support system for detection and management of Lung Abnormalities on a Chest X-ray in the following advantages:

Accurate diagnosis of Lung Abnormalities: The imaging AI can detect abnormalities in the lung that may be difficult for human experts to identify, while the language model can analyse patient history and related clinical data together to provide a more accurate diagnosis.

Personalized treatment recommendations: The language model can analyse patient history and other clinical data to provide personalized treatment recommendations that are tailored to the patient's specific needs and medical history. By taking into account the unique characteristics of each patient, the system can help to improve treatment outcomes and reduce the risk of complications.

Efficient use of healthcare resources: The system can help to streamline the diagnosis and treatment process, reducing the time and resources required to diagnose and treat lung disease. By providing accurate and timely diagnoses, the system can help to reduce the need for additional testing and treatments, which can be costly and time-consuming.

Monitoring disease progression: The system can be used to track changes in lung abnormalities over time, helping healthcare professionals to monitor disease progression and adjust treatment plans as needed. By providing regular updates on the patient's condition, the system can help to improve patient outcomes and reduce the risk of complications.

Overall, the system can help to solve a range of problems related to diagnosing and treating lung disease, improving the accuracy and efficiency of the clinical decision-making process and enhancing patient outcomes.

Various modifications to the embodiment will be readily apparent to those skilled in the art and the generic principles herein may be applied to other embodiments. However, one of ordinary skill in the art will readily recognize that the present disclosure is not intended to be limited to the embodiments illustrated but is to be accorded the widest scope consistent with the principles and features described herein.

The foregoing description shall be interpreted as illustrative and not in any limiting sense. A person of ordinary skill in the art would understand that certain modifications could come within the scope of this disclosure.

The embodiments, examples and alternatives of the preceding paragraphs or the description and drawings, including any of their various aspects or respective individual features, may be taken independently or in any combination. Features described in connection with one embodiment are applicable to all embodiments unless such features are incompatible.

The invention claimed is:

1. A system (100) for detecting lung abnormalities in a medical image (101), characterized in that, the system (100) comprises:

a server (104) comprising:

a memory (203);

a processor (201) coupled with the memory (203), wherein the processor (201) is configured to execute programmed instructions stored in the memory (203) to:

collect data corresponding to the medical image (101) and a patient clinical data (102);

identify lung abnormalities based on the collected data, using a hybrid machine learning system carried out by the processor (201), wherein the hybrid machine learning system is configured to perform steps of:

detecting lung abnormality by analysing the medical image (101) using an imaging model (207);

calculating an image confidence score corresponding to the detected lung abnormality;

extracting patient related information by analysing the patient clinical data (102) using a large language model (LLM) (208);

calculating a patient confidence score corresponding to the extracted patient related information;

generating an abnormality confidence score by combining the image confidence score and the patient confidence score; and generate an output, wherein the output corresponds to the lung abnormality with a comprehensive diagnosis and the abnormality confidence score.

2. The system (100) as claimed in claim 1, wherein the output corresponds to personalized treatment recommendation on patient medical history and clinical data.

3. The system (100) as claimed in claim 1, wherein the system (100) enables monitoring the lung abnormalities over time; wherein monitoring the lung abnormalities helps in tracking disease progression and adjustment of treatment plan.

4. The system (100) as claimed in claim 1, wherein the system (100) enables providing accurate and up-to-date lung abnormality diagnosis based on continuously learning from clinical evidence over time and adapting the system (100) accordingly.

5. The system (100) as claimed in claim 1, wherein the medical image (101) corresponds to chest image data in form of one of x-ray scans, CT scans, MRI scans, ultrasound images, and a combination thereof.

6. The system (100) as claimed in claim 1, wherein the patient clinical data (102) corresponds to one of patient history records, an electronic health records (EHR), clinical research data, updated medical device or healthcare guidelines available on public platforms and a combination thereof, wherein the clinical research data corresponds to research information published in domain of lung abnormalities.

7. The system (100) as claimed in claim 1, wherein the processor (201) of the server (104) is configured to train the imaging model (207) and the LLM (208) using the data collected by the processor (201) of the server (104).

8. The system (100) as claimed in claim 1, wherein the imaging model (207) corresponds to a deep learning algorithm, wherein lung abnormalities detected using the imaging model (207) corresponds to one of Asthma, Chronic obstructive pulmonary disease (COPD), Bronchiectasis, Bronchitis, pneumothorax, atelectasis, lung inflammation, Pulmonary fibrosis, Sarcoidosis, Lung cancer, Lung Infection (Pneumonia), Hyperinflation/Emphysema, Consolidation, Opacity, Scoliosis, Fibrosis, Tuberculosis screening, Atelectasis, Reticulo-nodular pattern, Nodules, Cavity, Calcification, Linear Opacities, Lung Nodule Malignancy, Covid-19 risk and a combination thereof.

9. The system (100) as claimed in claim 1, wherein the imaging model (207) is configured to calculate the image confidence score based on the analysis of the medical image (101).

10. The system (100) as claimed in claim 1, wherein the large language model (208) corresponds to Generative Pre-trained Transformer (GPT) model, wherein the patient related information extracted by the LLM (208) corresponds to one of identified risk factors, underlying cause of lung disease and a combination thereof, wherein the LLM (208) is configured to extract the patient related information from an unstructured clinical text and to provide treatment options.

11. A method (300) for detecting lung abnormalities in a medical image (101), characterized in that, the method (300) comprises:

collecting (301) data, by a processor (201) of a server (104), wherein the data corresponds to the medical image (101) and a patient clinical data (102);

analysing (302), by the processor (201) of the server (104) the collected data by using a hybrid machine learning system, wherein the hybrid machine learning system performs steps of:

detecting (303) lung abnormality by analysing the medical image (101) using an imaging model (207);

calculating (304) an image confidence score corresponding to the detected lung abnormality;

extracting (305) patient related information by analysing the patient clinical data (102) using a large language model (LLM) (208);

calculating (306) a patient confidence score corresponding to the extracted patient related information;

generating (307) an abnormality confidence score by combining the image confidence score and the patient confidence score; and generating (308), by the processor (201) of the server (104) an output, wherein the output corresponds to the lung abnormality with a comprehensive diagnosis and the abnormality confidence score.

12. The method (300) as claimed in claim 11, wherein the medical image (101) corresponds to chest image data in form of one of x-ray scans, CT scans, MRI scans, ultrasound images, and a combination thereof.

13. The method (300) as claimed in claim 11, wherein the patient clinical data (102) corresponds to one of patient history records, an electronic health records (EHR), clinical research data, updated medical device or healthcare guidelines available on public platforms and a combination thereof, wherein the clinical research data corresponds to research information published in domain of lung abnormalities.

14. The method (300) as claimed in claim 11, wherein the method (300) comprises training the imaging model (207) and the LLM (208) using the data collected by the processor (201) of the server (104).

15. The method (300) as claimed in claim 11, wherein the imaging model (207) corresponds to a deep learning algorithm, wherein lung abnormalities detecting using the imaging model (207) corresponds to one of Asthma, Chronic obstructive pulmonary disease (COPD), Bronchiectasis, Bronchitis, pneumothorax, atelectasis, lung inflammation, Pulmonary fibrosis, Sarcoidosis, Lung cancer, Lung Infection (Pneumonia), Hyperinflation/Emphysema, Consolidation, Opacity, Scoliosis, Fibrosis, Tuberculosis screening, Atelectasis, Reticulo-nodular pattern, Nodules, Cavity, Calcification, Linear Opacities, Lung Nodule Malignancy, Covid-19 risk and a combination thereof.

16. The method (300) as claimed in claim 11, wherein the large language model (208) corresponds to Generative Pre-trained Transformer (GPT) model, wherein the patient related information extracted by the LLM (208) corresponds to one of identified risk factors, underlying cause of lung disease and a combination thereof, wherein the patient related information is extracted from an unstructured clinical text and a treatment option recommended by the LLM (208).

17. The method (300) as claimed in claim 11, wherein the output corresponds to personalized treatment recommendation on patient medical history and clinical data.

18. The method (300) as claimed in claim 11, wherein the method (300) enables monitoring the lung abnormalities over time; wherein monitoring the lung abnormalities helps in tracking disease progression and adjustment of treatment plan.

19. The method (300) as claimed in claim 11, wherein the method (300) enables providing accurate and up-to-date lung abnormality diagnosis based on continuously learning from clinical evidence over time and adapting the method (300) accordingly.

* * * * *